(12) United States Patent
Beaty et al.

(10) Patent No.: US 6,227,856 B1
(45) Date of Patent: *May 8, 2001

(54) ABUTMENT AND COPING SYSTEM FOR USE WITH DENTAL IMPLANTS

(75) Inventors: Keith D. Beaty, Jupiter; Dan Paul Rogers, Royal Palm Beach, both of FL (US)

(73) Assignee: Implant Innovations, Inc., Palm Beach Gardens, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/012,256

(22) Filed: Jan. 23, 1998

Related U.S. Application Data

(60) Provisional application No. 60/036,046, filed on Jan. 27, 1997.

(51) Int. Cl.[7] .................................................. A61C 8/00
(52) U.S. Cl. ................................................ 433/172; 433/173
(58) Field of Search ................................... 433/172, 173, 433/174

(56) References Cited

U.S. PATENT DOCUMENTS

| | | | |
|---|---|---|---|
| 5,125,841 | 6/1992 | Carlsson et al. | 433/213 |
| 5,154,612 | 10/1992 | Carlsson et al. | 433/173 |
| 5,376,004 | 12/1994 | Mena | 433/173 |
| 5,417,568 | 5/1995 | Giglio | 433/173 |
| 5,476,382 | 12/1995 | Daftary | 433/172 |
| 5,564,924 | 10/1996 | Kwan | 433/173 |

FOREIGN PATENT DOCUMENTS 90 02 824   10/1990   (DE).

OTHER PUBLICATIONS

Product Catalog Prosthetics 1991, Brånemark System, Nobelpharma.

Guidelines Wide Platform, Brånemark System, 1996.

*Primary Examiner*—John J. Wilson
(74) *Attorney, Agent, or Firm*—Jenkens & Gilchrist

(57) ABSTRACT

A dental abutment forms an abutment post having a transmucosal base portion and a supragingival portion having a smaller transverse external cross-section than the proximal end of the base portion. The supragingival portion forms a through bore threaded at its proximal end and stepped to form an internal shoulder for seating the head of a screw for attaching the abutment post to the implant. The exterior surface of the abutment post forms a generally polygonal transverse cross-section for receiving hollow components having interior surfaces that can be telescoped over the abutment post. The abutment post is used in an abutment system that includes a healing cap, an impression coping and/or a prosthesis coping forming an interior surface that can be telescoped over the supragingival portion of the abutment post The opposed surfaces of the abutment post and the coping preferably have truncated corners that are very close to each other to maintain a coaxial relationship between the post and the coping, while the portions of the opposed surfaces adjacent to the truncated corners are spaced farther apart to permit limited angular movement of the post and coping relative to each other and to permit the entry of dental cement between the opposed surfaces.

20 Claims, 12 Drawing Sheets

ABUTMENT AND COPING SYSTEM FOR USE WITH DENTAL IMPLANTS

This application claims benefit of Provisional Appl. 60/036,046 filed Jan. 27, 1997.

FIELD OF THE INVENTION

The present invention relates generally to abutment and coping systems for use with dental implants to assist in the mounting and positioning of prostheses on the implant. This invention particularly relates to such abutment and coping systems that can be used in the restoration of a single tooth.

SUMMARY OF THE INVENTION

A primary object of this invention is to provide an improved abutment that permits a healing cap and/or an impression coping to be attached to the abutment by means of a screw that threads into the proximal end of the abutment.

Another object of this invention is to provide an abutment and coping system that (1) can be easily and efficiently made in a variety of different diameters and lengths, (2) permits the use of a common abutment post, in any given installation, to successively receive a healing cap, an impression coping and a prosthesis coping, and (3) permits the prosthesis coping to be attached to the abutment post with dental cement while being precisely centered on the abutment post and mechanically locked against substantial rotational movement relative to the abutment post.

A further object of this invention is to provide such an improved abutment and coping system that permits the prosthesis coping to be cemented to the abutment post while maintaining a precise coaxial relationship between the abutment and the coping.

Yet another object of the invention is to provide such an improved abutment and coping system that permits limited angular displacement of the prosthesis on the abutment, before the cement has cured, while maintaining a precise coaxial relationship between the prosthesis and the abutment.

Other objects and advantages of the invention will be apparent from the following detailed description and the accompanying drawings.

In accordance with the present invention, the foregoing objectives are realized by providing an improved dental abutment comprising an abutment post having a transmucosal base portion and a supragingival portion having a smaller transverse external cross-section than the proximal end of the base portion, the supragingival portion forming a through bore threaded at its proximal end and stepped to form an internal shoulder for seating the head of a screw for attaching the abutment post to the implant. The exterior surface of the abutment post preferably forms a generally polygonal transverse cross-section for receiving hollow components having interior surfaces that can be telescoped over the abutment post.

The abutment post is used in an abutment system that includes a healing cap, an impression coping and/or a prosthesis coping forming an interior surface that can be telescoped over the supragingival portion of the abutment post. At least a portion of the interior surfaces of the copings preferably forms a generally polygonal transverse cross-section with concave regions between the corners of the polygon for receiving dental cement for bonding the coping to the abutment post. The healing cap and/or the impression coping is preferably attached to the abutment by a screw that threads into the proximal end of the through bore in the abutment post. The opposed surfaces of the abutment post and the coping preferably have truncated corners that are very close to each other to maintain a coaxial relationship between the post and the coping, while the portions of the opposed surfaces adjacent to the truncated corners are spaced farther apart to permit limited angular movement of the post and coping relative to each other and to permit the entry of dental cement between the opposed surfaces.

BRIEF DESCRIPTION OF THE DRAWINGS

FIG. 21 is a side elevation, partially in section, of the analog shown in FIG. 1;

DETAILED DESCRIPTION OF PREFERRED EMBODIMENTS

Figure 1:
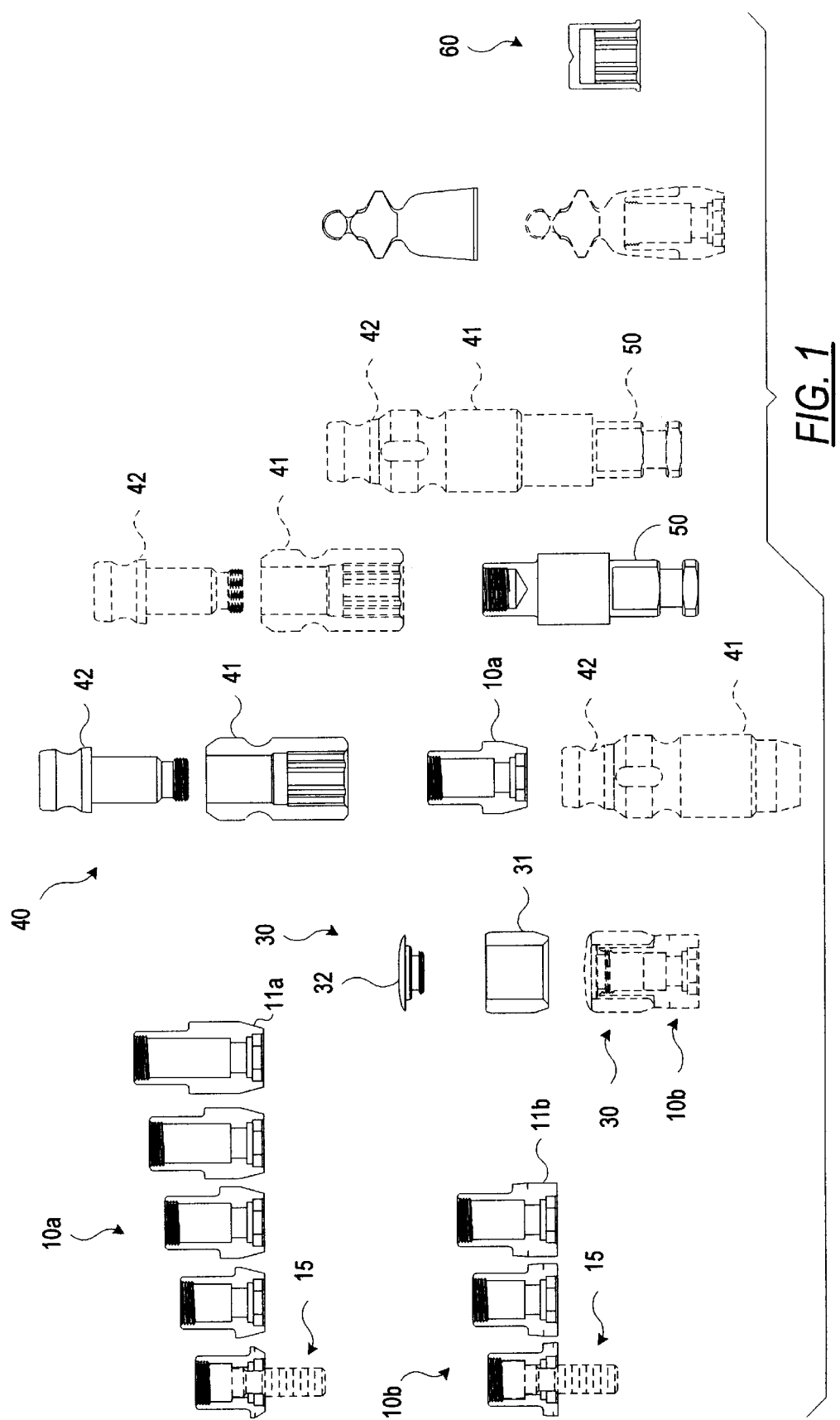
FIG. 1 is a family of side elevations of multiple components that can be used in the abutment system of this invention.

Turning now to the drawings and referring first to FIG. 1, there is shown a family of components for use in dental restoration procedures utilizing dental implants not shown. The dental implant itself may be any of the standard implants known in the art, preferably of the type that has a protruding hexagonal boss on the gingival end of the implant for fitting into a complementary hexagonal socket in the bottom of an abutment mounted on the implant. In FIG. 1, two sets of abutments 10a and 10b of varying lengths are provided for mounting on an implant, and each of these abutments has a hexagonal socket in the bottom surface thereof for fitting over a protruding hexagonal boss on the gingival end of an implant. The families of abutments shown in FIG. 1 include abutments having transmucosal sections of different lengths, to accommodate different gingival thicknesses in different patients. Two families of such abutments are shown in FIG. 1, the upper family having tapered (expanding in a supragingival direction) transmucosal sections 11a, and the lower family having straight, cylindrical transmucosal sections 11b.

Figure 3:
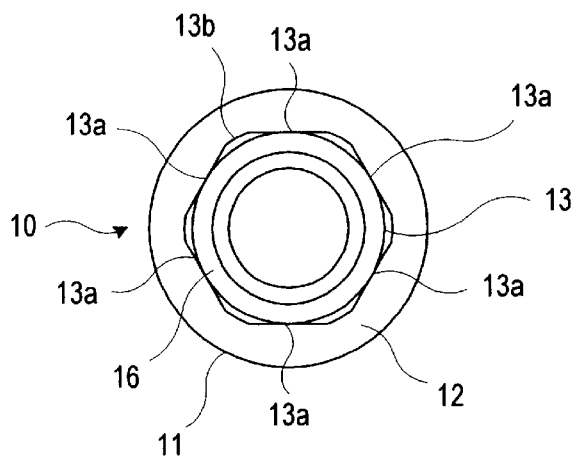
FIG. 3 is a top plan view of the abutment of FIG. 2.
Figure 4A:
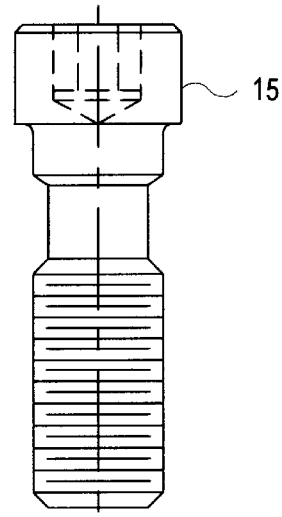
FIG. 4a is a side elevation of the screw used to attach the abutment of FIGS. 2–4 to a dental implant.
Figure 2:
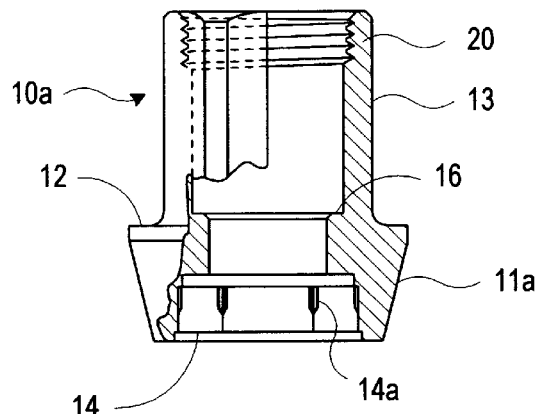
FIG. 2 is a side elevation, partially in section, of one of the abutments shown in FIG. 1.
Figure 4:
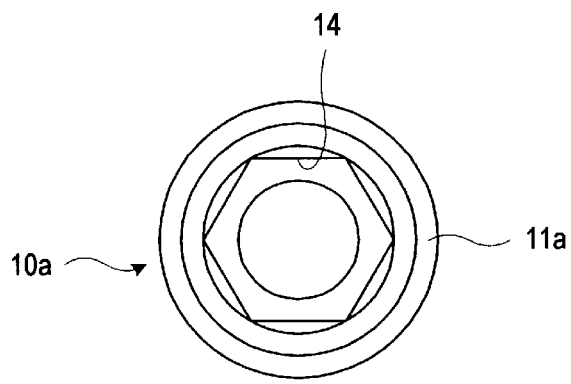
FIG. 4 is a bottom plan view of the abutment of FIG. 2.

One example of the abutments 10a is shown in more detail in the enlarged FIGS. 2 through 4. Referring to those figures, the abutment 10 has a transmucosal section 11a having a longitudinal dimension selected to extend through the patient's gingiva, from the gingival end of the implant to the outer surface of the gingiva. The tansmucosal section 11a terminates at an annular shoulder 12 which forms the transition between the transmucosal section 11a and a hollow post 13 having a transverse dimension smaller than that of the transmucosal section 11a. This post 13 ultimately receives a prosthesis coping on which the prosthesis (artificial tooth) is formed. In the plan view of FIG. 3, the post can be seen too have truncated corners 13b corresponding to 71 in FIGS. 27–28 and flat sides 13a corresponding to 73 in FIGS. 27–28.

The base of the abutment 10a forms a hexagonal socket 14 dimensioned to mate with the conventional hexagonal boss formed on the occlusal end of most dental implants. In the illustrative embodiment, the socket 14 includes integral corner shims 14a to prevent even small relative angular (rotational) movement between the abutment 10a and the implant, as described in more detail in pending U. S. patent application issued U.S. Pat. No. 5,725,375 and pending provisional patent application Serial No. 60/002,741, filed Aug. 24, 1995. To secure the abutment 10a to an implant, an abutment screw 15 (FIGS. 1 and 4a) is telescoped into a through bore extending through the abutment, so that the threaded shank of the screw protrudes from the distal end of the abutment and extends into a threaded hole in the occlusal end of the implant. The screw 15 is then threaded into the implant until the head of the screw is tightly seated on an internal annular shoulder 16 in the lower portion of the interior surface of the abutment 10a, thereby drawing the abutment into tight engagement with the implant.

In order to permit the use of screws to attach healing caps and impression copings to the abutment 10a, the interior surface of the abutment includes a threaded portion 20 at the proximal end of the through bore of the abutment Because the wall of the post 13 is relatively thin, the threads are preferably relatively narrow and shallow so that they do not cut through an excessive portion of the wall thickness.

Figure 6:
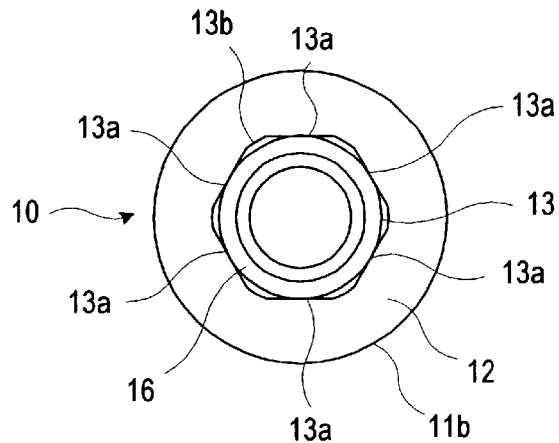
FIG. 6 is a top plan view of the abutment of FIG. 5.
Figure 5:
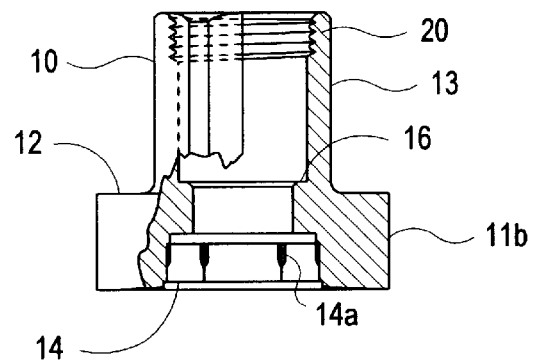
FIG. 5 is a side elevation, partially in section, of another of the abutments shown in FIG. 1.
Figure 7:
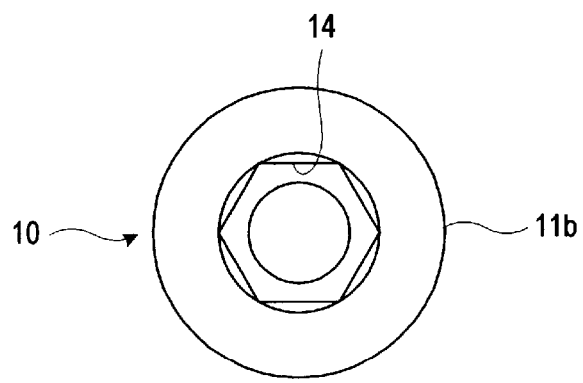
FIG. 7 is a bottom plan view of the abutment of FIG. 5.
Figure 9:
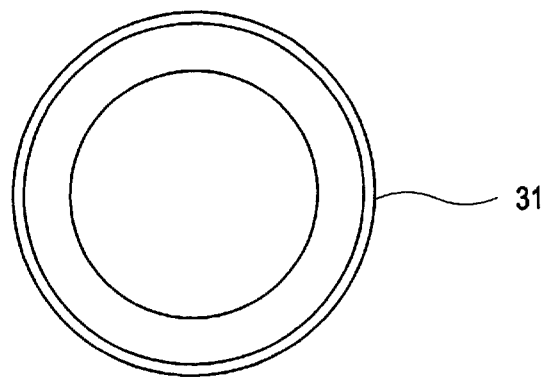
FIG. 9 is a top plan view of the healing cap of FIG. 8.
Figure 8:
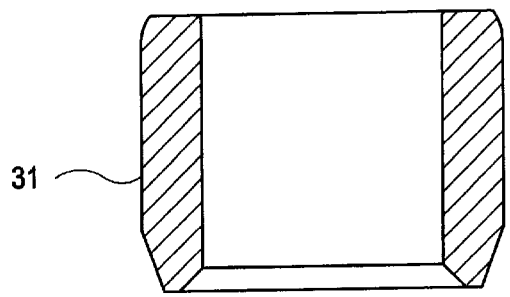
FIG. 8 is a vertical section of one of the healing caps shown in FIG. 1.
Figure 10:
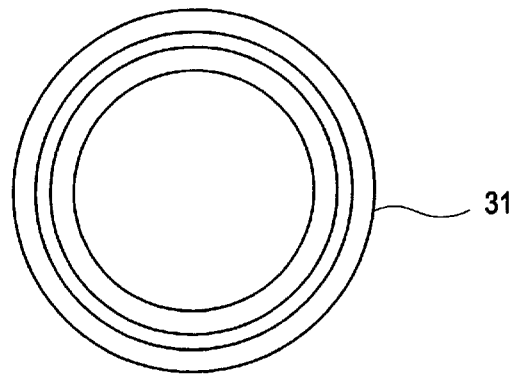
FIG. 10 is a bottom plan view of the healing cap of FIG. 8.
Figure 12:
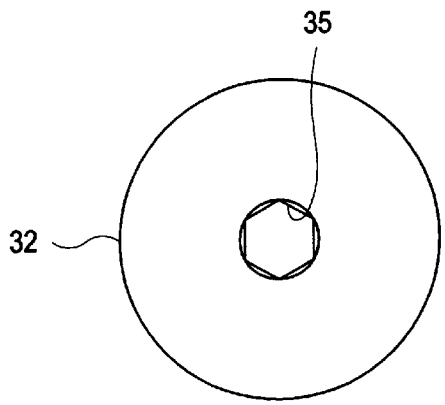
FIG. 12 is a top plan view of the healing cap screw of FIG. 11.
Figure 11:
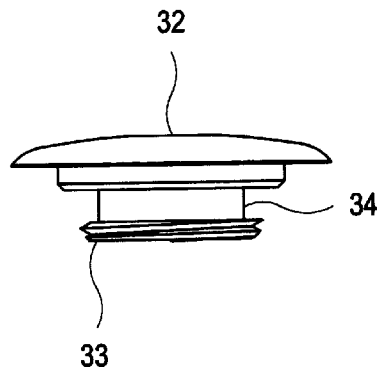
FIG. 11 is a side elevation of one of the healing cap screws shown in FIG. 1.
Figure 14:
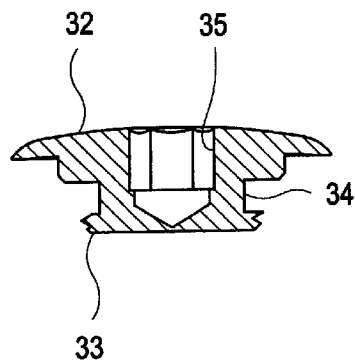
FIG. 14 is a vertical section of the healing cap screw of FIG. 11.
Figure 13:
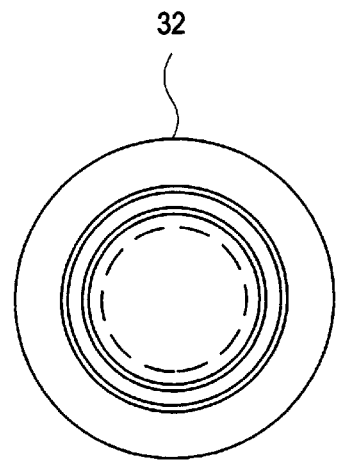
FIG. 13 is a bottom plan view of the healing cap screw of FIG. 11.
Figure 15:
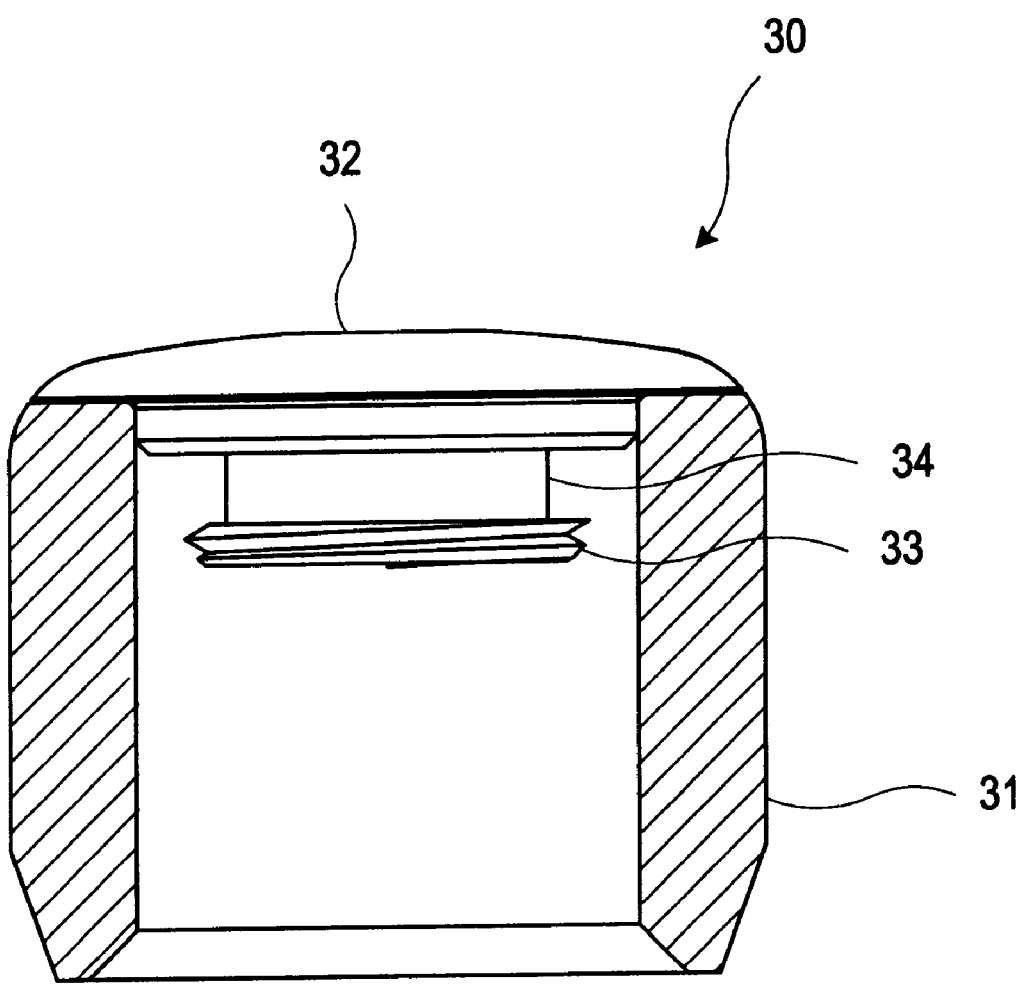
FIG. 15 is an assembly view of the healing cap of FIG. 8 and the healing cap screw of FIG. 11 after they have been assembled.
Figure 17:
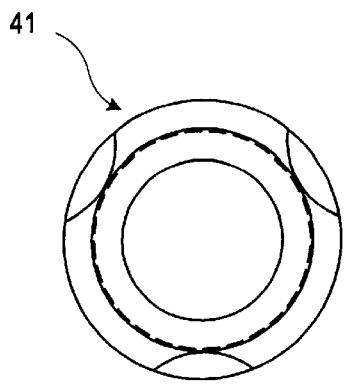
FIG. 17 is a top plan view of the impression coping of FIG. 16.
Figure 16:
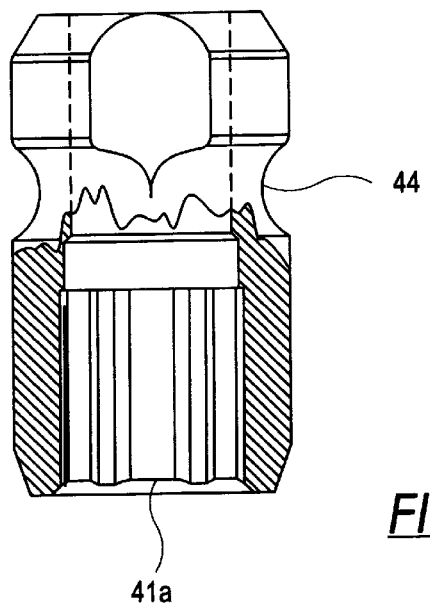
FIG. 16 is a side elevation, partially in section, of one of the impression copings shown in FIG. 1.
Figure 18:
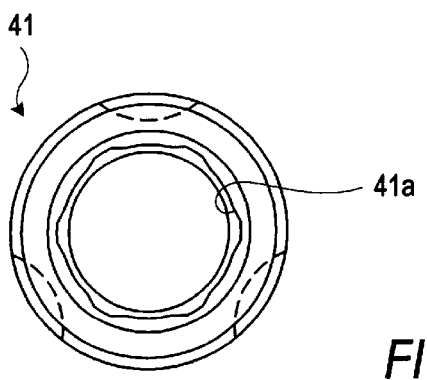
FIG. 18 is a bottom plan view of the impression coping of FIG. 16.
Figure 20:
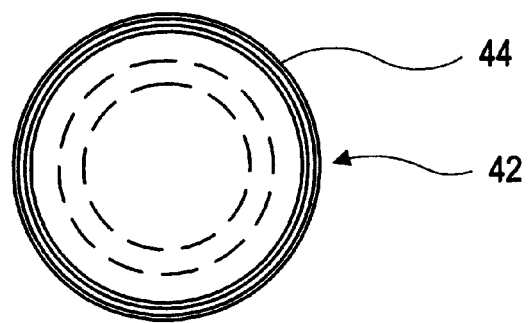
FIG. 20 is a top plan view of the impression coping screw of FIG. 19.
Figure 19:
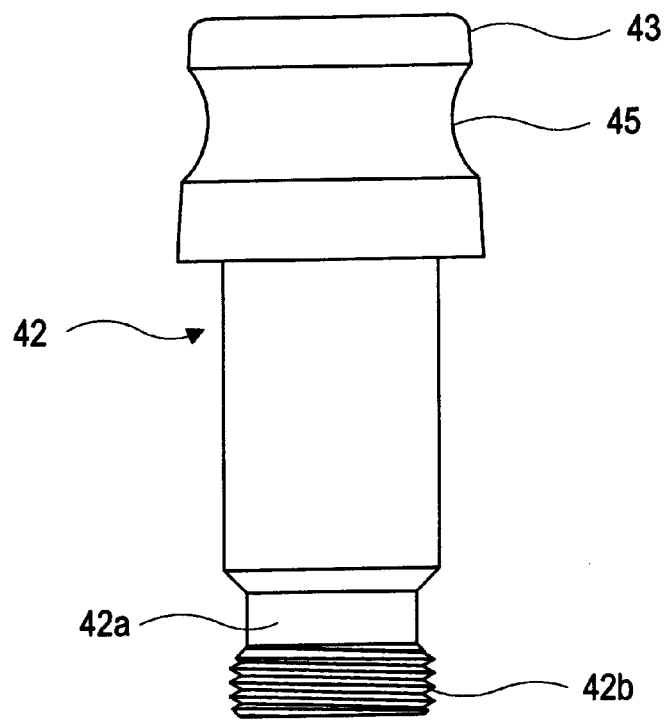
FIG. 19 is a side elevation of the impression coping screw shown in FIG. 1.

FIGS. 5 through 7 illustrate in more detail one of the abutments 10b having a straight cylindrical transmucosal section 11b. Except for its dimensions and the shape of the transmucosal section, this abutment is identical to the abutment described above in connection with FIGS. 2 through 4.

FIG. 1 shows a two-part healing cap 30, including a sleeve 31 and a screw 32, which are shown in more detail in FIGS. 8 through 15. The sleeve 31 has an inside diameter greater than the maximum transverse dimension of the post 13 so that the sleeve can fit over the post 13, with the distal end of the sleeve 31 coming to rest on the annular shoulder 12. The sleeve 31 is secured to the abutment by threading the shank of the screw 32 into the internally threaded portion 20 of the abutment post 13 until the head of the screw 32 tightly engages the proximal end of the sleeve 31, thereby pressing the sleeve 31 firmly against the shoulder 12. Of course, the threads 33 on the shank 34 of the screw 31 match those in the threaded portion 20 of the abutment post 13. A hexagonal socket 35 in the top of the screw 30 receives a wrench for installing the screw.

FIG. 1 also shows a two-part impression coping 40, including a hollow coping post 41 and an impression coping screw 42, which are shown in more detail in FIGS. 16 through 20. The interior surface 41a of the post 41 has a transverse cross-section that matches that of the exterior surface of the abutment post 13 so that the coping post 41 can telescope over the abutment post 13, with the distal end of the post 41 coming to rest on the annular shoulder 12. Because the matching transverse cross-sections of the two posts 13 and 41 are non-circular, the two posts are locked against any substantial rotation relative to each other. The post 41 is secured to the abutment by threading the distal end of the screw 42 into the internally threaded portion 20 of the abutment post 13 until the head of the screw 42 tightly engages the proximal end of the post 41, thereby pressing the post 41 firmly against the shoulder 12. As in the case of the healing cap screw, the threads 42b on the shank 42a of the screw 42 match those in the threaded portion 20 of the abutment post 13.

The head 43 of the screw 42 is elongated to form an extension of the post 41. The exterior surfaces of both the post 41 and the screw head 43 have recessed regions 44 and 45 extending around their circumferences to receive impression material. These recesses 44 and 45 merge smoothly with the adjacent surfaces to facilitate removal of impression material from the coping 40 when the coping is used as a transfer coping, i.e., the impression material is removed while the post 41 and the screw 42 remain temporarily attached to the implant The coping 40 is subsequently detached from the implant and transferred to the impression. It will be understood that this same coping post 41 can be used as a pickup coping by using a screw having a longer head that extends through the impression material, so that the screw can be removed from the coping before the impression material is removed from the patient. The coping post 41 is then picked up and removed from the patient along with the impression.

Figure 22:
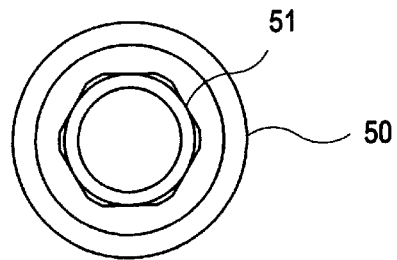
FIG. 22 is a top plan view of the analog of FIG. 21.
Figure 21:
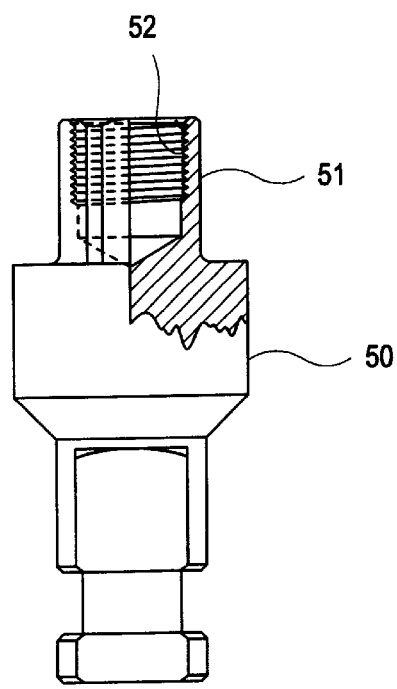
FIG. 21 is an enlarged transverse section taken through an assembly of the abutment of FIG. 2 and the impression coping of FIG. 16.
Figure 23:
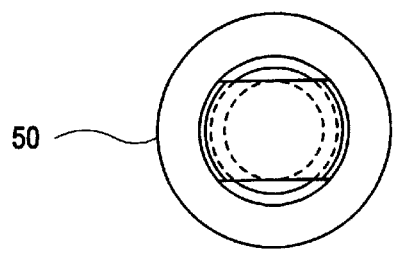
FIG. 23 is a bottom plan view of the analog of FIG. 21.

After the impression coping 40 has been removed from the patient, it may be attached to an implant analog 50 which is shown in FIG. 1, and in more detail in FIGS. 21 through 23. The post 51 of the analog 50 has the same exterior cross-sectional configuration as the abutment post 13, and the interior of the post 51 has a threaded portion 52 with the same threads used in the interior of the abutment post 13. As is well known, analogs are commonly used in the fabrication of dental prostheses, and fitting the analog 50 to the impression coping 40 ensures proper positioning of the prosthesis relative to the implant on which it is to be ultimately installed in the patient.

Figure 25:
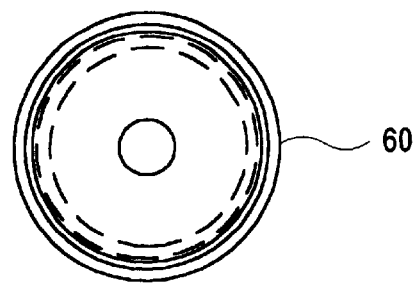
FIG. 25 is a top plan view of the prosthesis coping of FIG. 24.
Figure 24:
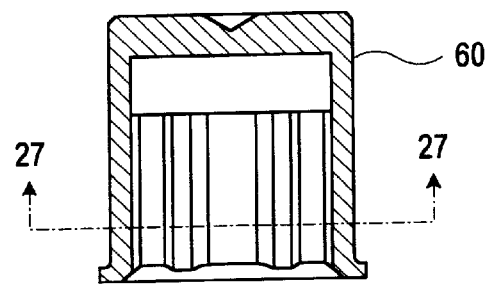
FIG. 24 is a vertical section of the prosthesis coping shown in FIG. 1.
Figure 26:
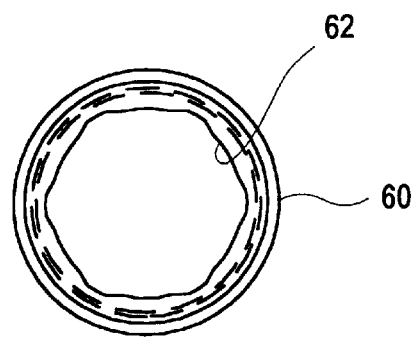
FIG. 26 is a bottom plan view of the prosthesis coping of FIG. 24.

The prosthesis is fabricated on a prosthesis coping 60, typically made of gold, which is shown in detail in FIGS. 24 through 26. The coping 60 is a hollow cylinder that is open at the distal end and closed at the proximal end. The interior 61 of the coping 60 is dimensioned and shaped to fit over the post 13 of the abutment 10, and the transverse cross-section of the interior surface of the coping 60 is substantially the same as the transverse cross-section of the impression coping post 41 described above.

Figure 27:
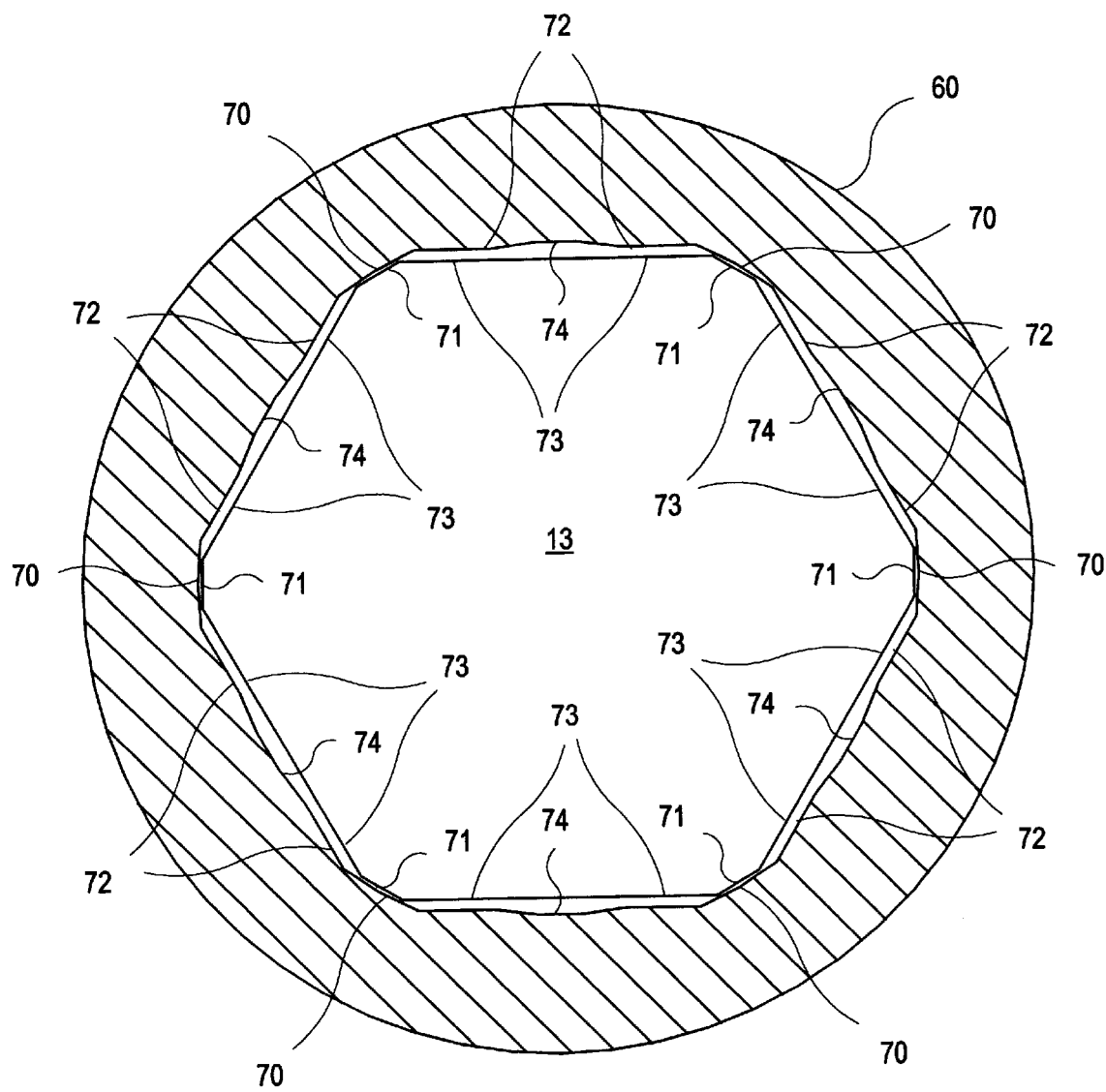
FIG. 27 is an enlarged section taken generally along line 27—27 in FIG. 24, and showing the configuration of the outer surface of the abutment of FIG. 2 inside the coping.
Figure 28:
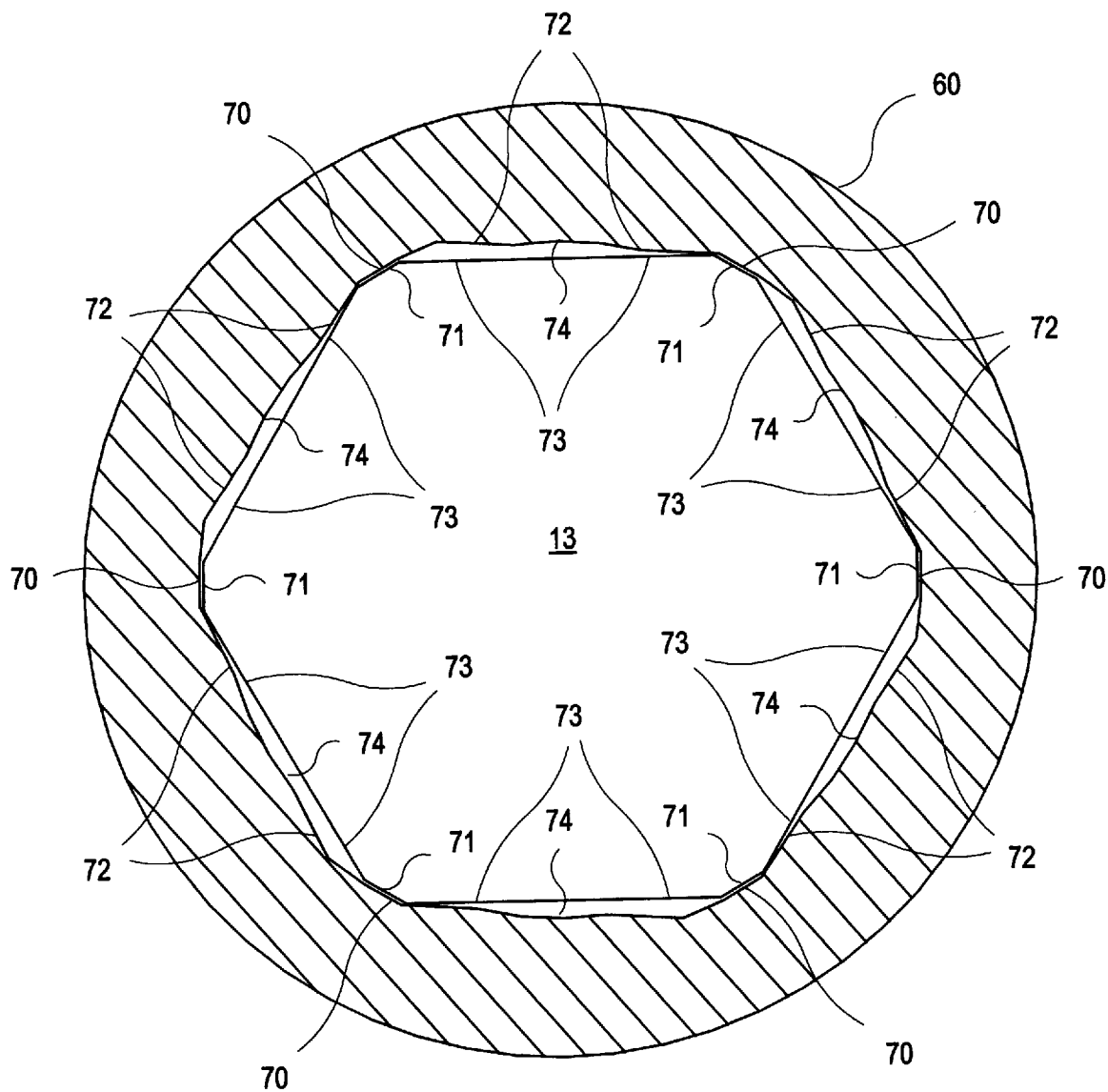
FIG. 28 is the same view shown in FIG. 27, with the coping and abutment rotated slightly relative to each other.

The configurations of the transverse cross-sections of the mating longitudinal surfaces of the abutment post 13 and either the impression coping 41 or the prosthesis coping 60 are preferably the configurations shown in the enlarged transverse sections shown in FIGS. 27 and 28. The opposed surfaces both have generally hexagonal configurations, with truncated corners 70, 71. The opposed surfaces formed by the truncated corners 70, 71 are very close to each other, e.g., about 0.001 inch apart, to maintain a precise coaxial relationship between the two components. The portions of the opposed surfaces 72, 73 adjacent to the truncated corners 70, 71 are spaced slightly farther apart, e.g., about 0.005 inch apart, to permit limited angular movement of the two components 13 and 60 relative to each other and to permit the entry of dental cement between the opposed surfaces. The precise coaxial alignment prevents a crown from moving laterally relative to the abutment, thereby preventing the bottom edge of the crown from overhanging the shoulder on the abutment. Yet, at the same time, the limited angular movement permitted by the wider spacing on opposite sides of the truncated corners permits the crown to be rotated slightly to the desired azimuthal position before the cement is cured to bond the crown permanently to the abutment. This limited angular movement of the crown relative to the abutment is illustrated in FIG. 28, which shows the coping 60 rotated several degrees in a counterclockwise direction relative to the abutment 13.

Between each pair of corners, the interior surface of the coping 60 forms an outwardly concave region 74 for receiving dental cement when the crown is cemented to the abutment 10. If desired, inwardly concave surfaces may be formed in the exterior surface of the abutment past between the corners of its hexagonal configuration.

What is claimed is:

1. An abutment in combination with a healing cap or impression coping for use with a dental implant, said abutment comprising an abutment post having a transmucosal base portion and a supragingival portion having a smaller transverse external cross-section than the proximal end of said base portion receiving said healing cap or impression coping, said abutment post forming a through bore that is stepped to form an internal shoulder for seating the head of a screw for attaching the abutment post to the implant, a proximal end portion of said through bore being threaded for receiving a screw attaching said healing cap or impression coping to said abutment post.

2. The abutment of claim 1 wherein the exterior surface of said supragingival portion of said abutment post forms a non-round transverse cross-section for preventing substantial rotation of said impression coping telescoped thereover.

3. The abutment of claim 2 wherein the exterior surface of said abutment post forms a generally polygonal transverse cross-section.

4. The abutment of claim 3 wherein said generally polygonal transverse cross-section forms corners which are truncated.

5. The abutment of claim 1 wherein said threaded proximal end portion of said through bore is spaced from said internal shoulder to allow space for a head portion of said screw.

6. An abutment system comprising the abutment post of claim 1, a healing cap or impression coping telescoped over said supragingival portion of said abutment post, and a screw attaching said healing cap, or impression coping to said abutment by threaded engagement with said threaded proximal end portion of said through bore.

7. The abutment system of claim 6 wherein said screw has a threaded shank for threading into said threaded portion of said through bore of said abutment post, and a head for engaging a proximal end surface of said selected member.

8. The abutment system of claim 6 wherein at least a portion of the opposed surfaces of said impression coping and said abutment post form complementary non-round transverse cross-sections for preventing relative rotation of those members.

9. An abutment system comprising the abutment post of claim 1 and a prosthetic coping telescoped over said supragingival portion of said abutment post, the opposed surfaces of said post and said coping having generally polygonal transverse cross-sections with truncated corners that are very close to each other to maintain a coaxial relationship between said post and coping.

10. An abutment-coping system for use with a dental implant, said system comprising
    an abutment post having a transmucosal base portion and a supragingival portion having a smaller transverse external cross-section than the proximal end of said base portion for receiving a coping,
    means for attaching the abutment post to the implant, and
    a coping having a hollow interior adapted to telescope over said supragingival portion of said abutment post, the opposed surfaces of said post and said coping having generally polygonal transverse cross-sections with truncated corners that are very close to each other to maintain a coaxial relationship between said post and coping, the portions of said opposed surfaces adjacent to said truncated corners being spaced farther apart to permit limited angular movement of said post and coping relative to each other and optionally to permit the entry of dental cement between said opposed surfaces.

11. The abutment-coping system of claim 10 wherein said abutment forms a through bore for passing a first screw through the abutment to the implant to attach the abutment to the implant, a proximal end portion of said through bore being threaded for receiving a second screw for optionally attaching said coping to said abutment post.

12. The abutment-coping system of claim 10 wherein said threaded proximal end portion of said through bore is spaced from said internal shoulder to allow space for a head portion of said first screw.

13. The abutment-coping system of claim 10 wherein said coping is a prosthesis coping.

14. A method of installing a dental prosthetic coping on a dental implant comprising the steps of
    attaching to the implant an abutment comprising an abutment post having a transmucosal base portion and a supragingival portion having a smaller transverse external cross-section than the proximal end of said base portion for receiving a coping, and telescoping over said supragingival portion of said abutment post a coping having a hollow interior, the opposed surfaces of said post and said coping having generally polygonal transverse cross-sections with truncated corners that are very close to each other to maintain a coaxial relationship between said post and coping, the portions of said opposed surfaces adjacent to said truncated corners being spaced farther apart to permit limited angular movement of said post and coping relative to each other and to permit the entry of dental cement between said opposed surfaces, and attaching said coping to said abutment post with dental cement.

15. An abutment system for use with a dental implant, said abutment system comprising an abutment post having a transmucosal base portion and a supragingival portion having a smaller transverse external cross-section than the proximal end of said base portion for receiving a healing cap, impression coping, or prosthetic coping, said abutment post forming a through bore that is stepped to form an internal shoulder for seating the head of a screw for attaching the abutment post to the implant, a proximal end portion of said through bore being threaded for receiving a screw for attaching said healing cap or impression coping to said abutment post, and a prosthetic coping telescoped over said supragingival portion of said abutment post, the opposed surfaces of said post and said coping having generally polygonal transverse cross-sections with truncated corners that are very close to each other to maintain a coaxial relationship between said post and prosthetic coping, the portions of said opposed surfaces adjacent to said truncated corners being spaced farther apart to permit limited angular movement of said post and coping relative to each other and to permit the entry of dental cement between said opposed surfaces.

16. An abutment system for use with a dental implant, said abutment system comprising an abutment post having a transmucosal base portion and a supragingival portion having a smaller transverse external cross-section than the proximal end of said base portion for receiving a healing cap, impression coping, or prosthetic coping, said abutment post forming a through bore that is stepped to form an internal shoulder for seating the head of a screw for attaching the abutment post to the implant, a proximal end portion of said through bore being threaded for receiving a screw for attaching said healing cap or impression coping to said abutment post, and a prosthetic coping telescoped over said supragingival portion of said abutment post, the opposed surfaces of said post and said prosthetic coping having generally polygonal transverse cross-sections with truncated corners that are very close to each other to maintain a coaxial relationship between said post and coping, at least one of said exterior surfaces of said abutment post and said interior surfaces of said prosthetic coping forms recesses for receiving dental cement for bonding said coping to said abutment post.

17. A method of installing a dental coping on a dental implant comprising the steps of attaching to the implant an abutment comprising an abutment post having a transmucosal base portion and a supragingival portion having a smaller transverse external cross-section than the proximal end of said base portion for receiving a healing cap, impression coping, or prosthetic coping, said abutment post forming a through bore that is stepped to form an internal shoulder for seating the head of a first screw for attaching the abutment post to the implant, a proximal end portion of said through bore being threaded for receiving a second screw for attaching said healing cap or impression coping to said abutment post, and telescoping a hollow prosthetic coping over said supragingival portion of said abutment post and attaching said prosthetic coping to said abutment post, wherein at least a portion of the opposed surfaces of said prosthetic coping and said abutment post form complementary non-round transverse cross-sections for preventing relative rotation of these members, said opposed surfaces forming generally polygonal transverse cross-sections, at least the inner surface of said pair of opposed surfaces having truncated corners and wherein at least one of said exterior surfaces of said abutment post and said interior surfaces of said prosthetic coping forms recesses for receiving dental cement for bonding said prosthetic coping to said abutment post.

18. The method of claim 17 which includes the step of attaching said impression coping to said post with a screw threaded into said threaded proximal end portion of said through bore, said screw having a head bearing against the proximal end of said coping.

19. The method of claim 17 wherein said threaded proximal end portion of said through bore is spaced from said internal shoulder to allow space for a head portion of said first screw.

20. The method of claim 17 wherein said coping is an impression coping, at least a portion of the opposed surfaces of said coping and said abutment post form complementary non-round transverse cross-sections for preventing substantial relative rotation of those members, and said impression coping is attached to said abutment post by said second screw threaded into said threaded proximal end portion of said through bore and having a head bearing against the proximal end of said coping.

\* \* \* \* \*